United States Patent [19]

Boettcher et al.

[11] Patent Number: 4,940,760
[45] Date of Patent: Jul. 10, 1990

[54] GROUP TRANSFER POLYMERIZATION PROCESS EMPLOYING SUPPORTED INITIATORS

[75] Inventors: Fritz P. Boettcher, Newark; Ira B. Dicker; Richard C. Ebersole, both of Wilmington, all of Del.; Walter R. Hertler, Kennett Square, Pa.

[73] Assignee: E. I. du Pont de Nemours and Company, Wilmington, Del.

[21] Appl. No.: 418,007

[22] Filed: Oct. 6, 1989

Related U.S. Application Data

[63] Continuation of Ser. No. 156,008, Feb. 16, 1988, abandoned.

[51] Int. Cl.$^5$ ............................. C08F 4/16; C08F 4/02; C08F 20/14
[52] U.S. Cl. ............................. 526/190; 526/192; 526/194; 526/221; 526/262; 526/286; 526/303.1; 526/312; 526/328; 526/329.7; 526/341
[58] Field of Search ............... 526/190, 192, 194, 201, 526/262, 303.1, 328, 329.7, 341, 221, 312

[56] References Cited

U.S. PATENT DOCUMENTS 4,588,795 5/1986 Dicker et al. ............... 526/192

OTHER PUBLICATIONS

Sogah et al., Group Transfer Polymerization. Polymerization of Acrylic Monomers, Macromolecules, 20, 1473, 1987.
Grubbs et al., Organometallic Polymers as Catalysts Organometallic Polymers, Carraher, Jr., et al., (ed), Academic Press, N.Y., N.Y., 129 (1978).

*Primary Examiner*—Joseph L. Schofer
*Assistant Examiner*—F. M. Teskin

[57] ABSTRACT

Group Transfer Polymerization (GTP) process for preparing a "living" polymer, the process comprising contacting under polymerizing conditions in a polymerization medium, at least one acrylic or maleimide monomer with an initiator which is a tetracoordinate organosilicon, organotin or organogermanium compound having at least one GTP initiating site and a catalyst which is or is a source of an anion selected from the group consisting of bifluoride, fluoride, cyanide, azide or a selected oxyanion, or a selected Lewis acid or Lewis base, the process further characterized in that the initiator or the anion or Lewis acid catalyst is chemically attached (grafted) to a solid support that is insoluble in the polymerization medium.

8 Claims, No Drawings

GROUP TRANSFER POLYMERIZATION PROCESS EMPLOYING SUPPORTED INITIATORS

This is a continuation of Ser. No. 07/156,008 filed on Feb. 16, 1988, now abandoned.

BACKGROUND OF THE INVENTION

1. Field of Invention

This invention relates to Group Transfer Polymerization employing supported initiators or catalysts.

2. Background

Preparation of "living" polymers by Group Transfer Polymerization (Webster et al., "Group Transfer Polymerization—A New and Versatile Kind of Addition Polymerization", J. Am Chem Soc., 105, 5706 (1983)) is well known Group Transfer Polymerization (GTP) methods are described in U.S. Pat. Nos. 4,414,372; 4,417,034; 4,508,880; 4,524,196; 4,581,428; 4,588,795; 4,598,161; 4,605,716; 4,622,372; 4,656,233; 4,659,782; 4,659,783; 4,681,918; 4,695,607; and 4,711,942; and in commonly assigned U.S. patent applications Ser. Nos 912 117 and 912 118 filed Sept. 29, 1986, now U.S. Pat. No. 4,732,955; 934,826 filed Nov. 25, 1986, now U.S. Pat. No. 4,783,500; 004,831 filed Jan. 13, 1987, now U.S. Pat. No. 4,822,859; 007,758 filed Jan. 27, 1987, now U.S. Pat. No. 4,806,605; and 048,958 filed May 19, 1987, now abandoned. These patents and patent applications disclose processes for polymerizing an acrylic or maleimide monomer to a "living" polymer in the presence of (i) an initiator having at least one initiating site and which is a tetracoordinate organo(Si, Sn or Ge) compound, including such a compound having at least one oxygen, nitrogen or sulfur atom attached to Si Sn or Ge; and (ii) a co-catalyst which is a source of fluoride, bifluoride, cyanide or azide ions or a suitable Lewis acid, Lewis base or selected oxyanion.

The aforesaid patents and patent applications also disclose capped, block, star and graft polymers prepared by GTP methods, and any of such polymers containing functional groups which are useful for further processing. Group Transfer Polymerization is further discussed in detail by Sogah et al. in Macromolecules, 20, 1473 (1987).

All of the aforesaid patents and patent applications employ initiators and catalysts (referred to also as co-catalysts) which are soluble to some extent in the polymerization solvent, if any, or in the monomers employed. It has until now been believed that such solubility was essential. The present invention provides an improved GTP process wherein the initiator or the catalyst is chemically attached (grafted) to an insoluble support material, thus facilitating separation and recovery of the "living" polymeric product and of the initiator or catalyst. In a preferred embodiment, the "living" polymer remains grafted to the support.

Use of catalysts or initiators which are supported on insoluble materials in synthetic reactions, including non-GTP polymerizations, are known. A. Akelah et al., Chem. Revs., 81, 557 (1981) review the application of functionalized polymers in organic synthesis. Functionalized polymers are defined as synthetic macromolecules to which are chemically bound functional groups which can be utilized as reagents, catalysts, etc. A wide variety of polymer-supported catalysts and their uses in organic synthesis are described. Ionic catalysts wherein the cation is chemically bound to a polymeric support, such as polystyrene, are disclosed; e.g. $PS-(CH_2)_nN(R)_2R'X^-$ wherein PS is polystyrene, n is 0 or 1-3, R and R' are hydrocarbyl and X can include F, Cl, Br, OCN and OH.

Hellstern et al., Polymer Preprints (Am. Chem. Soc., Div. Poly. Chem.),28 [2], 328 (1987)) disclose the preparation of a soluble methacrylate-functional macromonomer by reacting poly(dimethyl siloxane) with 3-methacryloxypropyldimethylchlorosilane, and conversion of the macromonomer to a graft copolymer by GTP employing a silyl ketene acetal initiator and an acetate catalyst.

G. Cainelli et al., Synthesis Communications, Nov. 723 (1975) disclose anion exchange resins which are useful as catalysts in many organic reactions. The resins contain quaternary ammonium cations chemically bonded to a macroreticular resin such as Amberlite IRA-904; counter anions include oxyanions such as carboxylate.

T. Mukaiyama et al., Chemistry Letters (Japan), 1363 (1985) disclose aldol reactions of acetals and silyl enol ethers catalyzed by polystyrene-supported trityl perchlorate, forming beta-keto ethers.

J. F. W. Keana et al., J. Org. Chem., 51(10), 1641 (1986) describe the immobilization of biologically active materials, such as cholesterol or 1-adamantanamine, by reaction with chlorocarbonate-derivatized silica gel.

M.A. Askarov et al., Vysokomol. Soedin., Ser. B., 15{9}, 650 {1973); Chem. Abstracts 80(16):83714m disclose initiation of vinyl monomer polymerization, including methyl methacrylate, by heating in water in the presence of trialkylammonium salts of chlorinated styrene-divinylbenzene copolymers.

U.S. Pat. No. 4,232,141 discloses polymerization of vinyl chloride in aqueous medium using a water-insoluble polymerization initiator; the initiator is well dispersed in the polymerization medium.

Immobilization of biologically active materials, such as enzymes, on insoluble macromolecular supports is well known.

International Publication No. WO 86/01514 discloses solid phase synthesis of oligonucleotides wherein the first monomer unit is attached to the solid phase by a urethane bridge.

U.S. Pat. No. 4,574,060 discloses the dimerization of acrylonitrile to 1,4-dicyano-1-butene using a cross-linked polystyrene bound diarylphosphinite catalyst of the formula Polymer-$C_6H_4$-P(OR)Ar wherein Polymer is polystyrene crosslinked with 1% of divinylbenzene, R is alkyl and Ar is substituted phenyl.

The surface properties of polymeric materials are important in many industrial, electronic, biotechnology and medical applications, particularly those applications depending on molecular interactions at the interface between the surrounding media and the bulk polymer.

The bulk properties of polymers are known to influence their mechanical properties and molecular structure. Often, however, the average bulk chemical properties are unsuited to the desired surface requirements for specific applications. For example, the molecular composition required for structural strength may differ from that required for biocompatibility, dye retention, chemical reactivity or inertness. Furthermore, surface chemical properties may be changed by external factors such as orientation, oxidation, contamination and fabrication.

Several coating and grafting techniques have been developed in the art for selective modification of surface properties, including:

Ionizing Radiation Grafting (e.g. UV, gamma ray, electron beam);

Chemical Grafting (e.g. ceric ion reactions with —OH);

Peroxide Reactions (e.g. thermal and chemical activation);

Active Vapor Reactions (e.g. RF and microwave plasma);

Anionic Grafting (e.g. metal halogen formation);

Cationic Grafting (e.g. aluminum alkyl initiated reactions);

Ziegler—Natta Reactions; and

Polycondensation Coupling Methods.

Each of the above methods can provide surfaces which differ substantially from the bulk polymer in both chemistry and morphology. However, each method is limited in its capacity to tailor surface properties for a specific application, by (i) the nature of the polymerization reaction and the inherent control provided therein; and/or (ii) the solubility and molecular mobility (fluidity) of the bulk polymer.

The art methods do not permit sufficient control over graft polymer structure, composition and functionality for many important uses. Moreover, the art grafting methods normally require substantial polymer fluidity, which makes it difficult or impossible to graft molecules thereto with the required degree of molecular orientation.

To maintain control over the spatial orientation of graft polymers, it is important that the grafting method provide for covalent coupling of graft material to a rigid support. Furthermore, the grafting method should function on insoluble and highly crosslinked bulk polymers which do not swell or solubilize in the presence of monomers, solvents, and/or reagents used in the grafting process or in use. With many art grafting methods, especially radiation grafting, a fluid bulk phase is essential to insure monomer contact with free radicals. As radical formation is mass dependent, radical concentration at the surface tends to be low, and hence retention of molecular orientation is poor.

An object of this invention is to provide additional techniques for carrying out Group Transfer Polymerization. Another object is to provide grafting technology which affords improved control over, and means of manipulating, the molecular structure, composition, orientation and surface properties of the resultant grafted polymer.

SUMMARY OF THE INVENTION

The invention provides a Group Transfer Polymerization (GTP) process for preparing a "living" polymer, the process comprising contacting under polymerizing conditions in a polymerization medium, at least one acrylic or maleimide monomer with an initiator which is a tetracoordinate organosilicon, organotin or organogermanium compound having at least one GTP initiating site and a catalyst which is, or is a source of, an anion selected from the group consisting of bifluoride, fluoride, cyanide, azide or a selected oxyanion, or a selected Lewis acid or Lewis base, the process further characterized in that either, but not both, the initiator or the anion or Lewis acid catalyst is chemically attached (grafted) to a solid support that is insoluble in the polymerization medium. By "a solid support that is insoluble in the polymerization medium" is meant a solid support material from which no detectable amount, using commonly available analytical techniques, is dissolved by exhaustive extraction with the polymerization medium. The invention also provides: GTP "living" polymer grafted to the initiator support; GTP initiator that is chemically attached (grafted) to an insoluble support; and process for preparing such a GTP initiator.

DETAILED DESCRIPTION OF THE INVENTION

In this invention either the GTP initiator having at least one GTP initiating site, or the GTP catalyst, both as described above, is chemically bonded to an insoluble support. Supports for the initiator or the catalyst may be organic materials, such as synthetic polymers, or inorganic materials, such as silica or a zeolite. Preferred supports for both initiator and catalyst are synthetic polymers, most preferably crosslinked polymers, such as polystyrene or polydimethylsiloxane resins. The essential requirements for a support are that it be insoluble in the polymerizing medium and that it contain or can be chemically treated to contain: (i) functional chemical groups which are GTP initiating sites or which can react with appropriate chemical compounds to form GTP initiating sites; or (ii) functional chemical groups which are cationic moieties or which can react with appropriate chemical compounds to form cationic moieties.

In summary, the process for preparing an insoluble Group Transfer Polymerization (GTP) initiator that contains at least one GTP initiating site and is chemically attached (grafted) to an insoluble solid support comprises contacting and reacting:

A. (1) a suitably functionalized support;

(2) a soluble tetracoordinate organosilicon, organogermanium or organotin compound that is a GTP initiator having at least one GTP initiating site; and (3) a catalyst that is a source of fluoride, bifluoride, cyanide or azide ions or a suitable Lewis acid or selected (bi)oxyanion; or B. (1) a suitably functionalized support; and (2) a soluble tetracoordinate organosilicon, organogermanium or organotin compound that is a precursor to a GTP initiator having at least one GTP initiating site; or C. (1) a GTP initiator precursor that is a saturated or $\alpha,\beta$-ethylenically unsaturated ester or nitrile; and (2) a support having at least one functional group selected from hydrosilyl, hydrogermyl, hydrostannyl, halosilyl, halogermyl and halostannyl, the functional group(s) having one or two substituents selected from H and Cl; provided, however, the support having the hydrosilyl, hydrogermyl or hydrostannyl functional group is contacted and reacted with the GTP initiator precursor in the presence of a hydrosilylation, hydrogermylation or hydrostannylation catalyst.

The immediately following description is directed to that embodiment of the invention wherein the GTP initiator is chemically attached to an insoluble (in the polymerization medium) support.

The support is an insoluble material to which is chemically attached (grafted) a GTP initiator of the type described in the aforesaid patents and patent applications, the disclosures of which are hereby incorporated by reference. A description of the monomers and the catalysts may also be found in the aforesaid patents and patent applications. Additionally, it has been found that vinyl sulfones are useful monomers in the process of this invention. The product resulting from carrying out the process of the invention with a supported initiator is a GTP "living" polymer that is chemically attached to the support. If the initiator is attached to the support through its silicon, germanium, or tin atom which is the "transfer group", the grafted polymer can easily be removed from the insoluble support material (e.g. for characterization purposes) and, in fact, may become detached in the presence of adventitious protonic compounds.

The insoluble materials with chemically attached GTP initiating sites can be prepared by reacting an insoluble support material containing suitable functional groups with a soluble GTP initiator or a precursor thereof. The soluble GTP initiator, its precursor, or the functional groups in the support provide the tetracoordinate silicon-, germanium- or tin-containing moiety which is the essential component of a GTP initiating site. Preferably, such moiety is present in the soluble GTP initiator or its precursor.

When the tetracoordinate silicon-, germanium- or tin-containing moiety is present in the soluble GTP initiator or precursor, reaction of the soluble GTP initiator with the functional groups in the support material requires a catalyst which is soluble in the reaction medium and is, or is a source of, fluoride, bifluoride, cyanide or azide ions or a suitable Lewis acid or selected (bi)oxyanion. Suitable Lewis acids or selected (bi)oxyanions are those described in the aforesaid GTP patents and patent applications. Suitable functional groups in the support materials include those of the formula —RX wherein R is a single bond or $C_{1-10}$, preferably $C_{1-4}$, aliphatic hydrocarbylene and X is selected from —Cl, —Br, —I, —CHO, —CN and —OC(O)C(Y)=CH$_2$ wherein Y is H or methyl. It will be understood by one skilled in the art that other functional groups, such as —Li, —OH, —CO$_2$H, —CO$_2$R', —OCOR' and —CONHR'R" wherein R', and R", independently, are selected from $C_{1-4}$ alkyl, which are convertible by known methods to the suitable functional groups such as —RX can be employed, provided the appropriate conversion reactions are performed first. With the final four groups listed in the preceding sentence, in situ conversion to a transitory lithium enolate intermediate is required, the enolate then reacting with a soluble GTP initiator precursor to form the insoluble supported GTP initiator product. Typical conversion reactions are illustrated in Examples 10A and 23A wherein chloromethylated crosslinked polystyrene is employed as the insoluble support. In these experiments, —CH$_2$Cl groups are converted in a series of steps to —ROCOR' group wherein R' is isopropyl and R is —CH$_2$CH$_2$—(Example 10A) or —CH$_2$—(Example 23A), followed by low temperature reaction with a lithium amide to form a lithium enolate intermediate which then reacts with a soluble GTP initiator precursor, trimethylsilyl chloride, to form the insoluble supported GTP initiator product. A monomer such as 3-(dimethylchlorosilyl)propyl methacrylate can be reacted with a hydroxyl or lithiated support material and the resulting grafted monomer can be converted to an initiator by reaction with a silyl cyanide or with a monomeric or polymeric silyl ketene acetal. In general, the conversion reactions can be carried out in situ prior to preparing the insoluble supported initiator without removing solvents or by-products.

A preferred functionalized support is chloromethylated crosslinked polystyrene wherein the —Cl in the chloromethyl groups can readily be converted to any of the above-listed suitable functional groups by known methods The choice of functional group in the support depends on the composition of the soluble GTP initiator or precursor employed and whether a permanent or temporary grafting link is desired.

Examples 4A and 26 illustrate the preparation of an insoluble supported GTP initiator, from crosslinked polystyrene wherein the suitable functional group is chloromethyl, by reaction with a bis(silyl ketene acetal) in the presence of a GTP anion- or Lewis acid-catalyst. A similar reaction occurs when the support material contains —CHO groups. Temperatures of about 0° C to about 150° C are suitable for these reactions. An insoluble supported GTP initiator can also be prepared directly from crosslinked polystyrene containing —RCN functions, such as cyanomethyl, by reaction with a soluble silyl, germyl or stannyl ketene acetal GTP initiator, or by low temperature silylation, germylation or stannylation via a lithium enolate using a lithium amide and chlorotrimethylsilane, chlorotrimethylgermane or chlorotrimethylstannane, as described in the preceding paragraph. If a chain transfer agent, such as described in U.S. Pat. No. 4,656,233, supra, is attached to the insoluble support material, then Group Transfer Polymerization of an acrylic monomer in the presence of such a chain transfer agent-containing support will produce a supported (grafted) polymer. Such a chain transfer agent can be prepared, for example, by reaction of chloromethylated crosslinked polystyrene with tetraethylammonium cyanide.

In the preparation of insoluble supported initiators of the invention from support materials having functional groups which contain tetracoordinate silicon, germanium or tin moieties, such groups should also contain one or two active halogen or hydrogen atoms, that is, the functional groups should comprise halosilyl, halogermyl or halostannyl groups, or hydrosilyl, hydrogermyl or hydrostannyl groups. These functional groups are reacted with a soluble GTP initiator precursor, that is, a saturated or $\alpha,\beta$-ethylenically unsaturated ester or nitrile. When the support contains halogenated functions, the soluble ester or nitrile should first be converted in situ to a lithium enolate intermediate which then reacts with the support functions to form the supported GTP initiator. When the support functions contain hydrogen, a hydrosilation, hydrogermylation or hydrostannylation catalyst, as the case may be, such as a strong acid, a source of free radicals or, preferably, a compound containing a noble metal, such as rhodium, platinum or gold, is required. The catalysts should be soluble in the reaction medium.

In an alternative procedure, a soluble support having functional groups containing tetracoordinate silicon, germanium or tin may be reacted as described in the foregoing passage with a GTP precursor that is an ethylenically unsaturated ester or nitrile, provided that the precursor contains at least three equivalents of ethylenic unsaturation per mole of precursor so as to provide GTP initiating sites and crosslink, and hence insolubilize, the support. Examples 27 and 28 illustrate the preparation of insoluble supported GTP initiators from support materials having hydrosilyl and chlorosilyl functional groups, respectively. In addition to the methods disclosed in the examples herein, silyl cyanides or sulfides can be prepared from insoluble materials containing chlorosilane groups, by reaction of the chlorosilane groups with cyanide ions or alkyl or aryl mercaptides. Such supported silyl cyanides or sulfides are suitable GTP initiators in the process of this invention.

The insoluble supported GTP initiators of the invention are prepared in a suitable medium which may be selected from solvents disclosed in the aforesaid GTP patents and patent applications. It will readily be understood that the medium selected will be a solvent for the monomer and the catalyst, even though it is not a solvent for the insoluble support material. Reaction temperatures are in the range of about $-100°$ to about $150°$ C. When a lithium enolate intermediate is prepared as described above, temperatures below about $-20°$, preferably below about $-60°$ C, are required. Other reactions are preferably carried out at temperatures above $0°$ C. The soluble GTP initiator or precursor is normally employed in a molar ratio to the functional groups of about 1:1 to about 1:10, preferably about 1:1 to about 1:4. Hydrosilation catalyst concentration (required for hydrosilyl, hydrogermyl or hydrostannyl functional groups) should be in the range of about 0.01 to about 1.0, preferably about 0.05 to about 0.5, mole per mole of precursor.

The insoluble materials may be polymers, minerals, metals (often with oxide coatings), pigments, metalloids, chromatographic materials, biomaterials, or composites. The insoluble materials may be in particulate form or in the form of specific shapes.

After the initiator or initiator-precursor has been attached to the insoluble material, the polymerization can be carried out by exposing the treated insoluble material, in the presence of a GTP catalyst, to the monomer to be polymerized, in solution or dispersion, or without solvent, or in the gas phase. Grafted block copolymers can be prepared by sequential exposure to a plurality of monomers. If grafted random copolymers are desired, then the treated insoluble material may be exposed to a mixture of a plurality of monomers. Exposure to polyfunctional monomers will result in, for example, grafted branched polymers or cyclopolymers. If monomers containing functional groups are used, then the resulting grafted polymers will contain these functional groups. Such functional groups may be used, for example, to introduce additional grafted polymers or functionality.

The polymerizations can be carried out over the temperature range disclosed in the aforesaid patents and patent applications, but for convenience, temperatures of ambient or above are preferred. In the case of polymerization of acrylonitrile in dimethylformamide (DMF) solution, low temperatures (e.g. $-50°$ C) are preferred. The polymerizations usually proceed somewhat more slowly than an analogous polymerization performed under homogeneous conditions as in the examples of the aforesaid patents and patent applications. The use of solvents is optional, since neat monomer can be used, as can gaseous monomer (provided that the solid initiator has been treated with catalyst). If a solvent is used, it should be an aprotic liquid selected from the solvents described in the aforesaid patents and patent applications. It is generally advantageous to select a solvent which will swell the grafted polymer to maximize the rate of polymerization. The amount of solvent relative to the insoluble initiator should be such that stirring is convenient. However, in some cases, stirring may not be desirable or even possible (as when the insoluble material comprises a large surface area). The solvent may also be selected so as to facilitate wetting of the surface of the insoluble material.

When liquid and solid phases are present during the carrying out of the invention process, the systems are heterogeneous, and isolation of the grafted products is easily accomplished by filtration or by mechanically removing the solid from the liquid phase. When gaseous monomers are used, no isolation is required. However, the product can be purified by rinsing with a liquid or by extraction with a liquid (as in a Soxhlet apparatus). Depending on the monomers used, the surfaces of the insoluble initiators can be rendered hydrophilic or hydrophobic, hard or soft, by the growing polymers, or numerous other characteristics can be altered, as will be obvious to one skilled in the art. When the initiator is bonded to the insoluble material through the silicon, germanium, or tin atom as noted above, the resulting grafted polymer can be removed from the support by treatment with a chain transfer agent in the presence of a catalyst, as described in U.S. Pat. No. 4,656,233, supra. The solid initiator is thereby regenerated and is reusable to initiate another polymerization. This particular aspect of the process permits the use of the insoluble initiator as a column packing, or in a fluidized bed, for the controlled formation of grafted polymers which can then be removed by the chain transfer process. The packing or bed is then regenerated and is reusable. For many applications it is desirable to leave the "living" polymeric product grafted to an insoluble support. For such applications, initiators bonded to the insoluble support material through stable links such as carbon-carbon or carbon-oxygen bonds are employed (see, e.g., Examples 10A, 23A and 26). The grafted "living" polymers can then be further polymerized with functional monomers, or capped with functionalized capping agents, as described in the aforesaid patents and patent applications, providing functionalized terminal blocks or units which can be used for specialized reactions such as the immobilizing of biologically active materials (Examples 29-31).

The concentrations of soluble catalyst and of liquid monomers employed in the present process relative to insolubilized initiator are those described in the aforesaid patents and patent applications. Gaseous monomers can be employed at much lower concentrations than liquid monomers.

In the alternative mode of the invention, the process of the invention employs a conventional, soluble GTP initiator and the GTP catalyst is chemically attached to the insoluble support. In this embodiment, as noted above, the catalyst is or is a source of a selected oxyanion, fluoride, bifluoride, cyanide, or azide, or a selected Lewis acid.

More specifically, the anion of the GTP catalyst is rendered insoluble in the reaction medium by its attachment to a counter ion (cation) which, in turn, is chemically attached to the insoluble support. The counter ion can be a quaternary ammonium, sulfonium, phosphonium, or arsonium ion. The support is preferably polymeric and completely insoluble in the polymerization medium. The insolubility is most commonly conferred by crosslinking. Catalytic activity is generally greater when crosslink density is low and the polymeric support is swelled by the liquid reaction medium.

Numerous polymeric supports are suitable for use in the invention process, such as polystyrenes, polyamides, polyesters, polyvinylpyridinium salts, polyethylene oxides, polyethers, acrylic polymers, polysulfones, polyolefins and polysulfides. The polymeric support must be insoluble in the polymerization medium, and this insolubility may be achieved by crosslinking, as indicated above. When used in conjunction with the catalyst, the polymeric support, if not inherently a polycation such as a polyvinylpyridinium salt, must be functionalized to provide a covalently bound cation to serve as the counter ion for the catalytic anion. Many methods for such functionalization of polymers have been described in the literature, for example, Akelah and Sherrington, *Chem. Rev.*, 81, 557 (1981); Manecke and Storck, *Angew. Chem., Int. Ed. Engl.*, 17, 657 (1978); and Darling and Frechet, *J. Org. Chem.*, 51, 2270 (1986). Technology for covalent functionalization of minerals with quaternary ammonium salts has been described by Arkles, *Chemtech*, 7, 766 (1977). Example 13 herein provides a special case where the catalyst is attached directly to the silicon atom of a supported silyl ketene acetal for use in polymerization of gaseous monomers.

Since reactions catalyzed by insoluble catalysts often proceed more slowly than the corresponding homogeneous catalyzed reaction, it is usually desirable to design the system so that a polymer-supported catalyst is swelled by the reaction medium to increase the rate of diffusion of reactants to the catalytic sites. Thus, if a swellable support is used, the reaction rate can be increased by choosing a reaction medium which will swell the support.

The general conditions for carrying out the polymerizations using the insolubilized anion catalysts are the same as those for the homogeneous polymerizations described in the aforesaid patents and patent applications with respect to temperature, solvent, initiator, and monomer. The amount of insolubilized catalyst to be used depends on the amount of catalytic anion on the support (generally expressed as millequivalents per gram of polymer). The catalyst will generally be operable in the same concentration range as described for the homogeneous systems. If the support is nonswellable, higher concentrations of catalyst are desirable.

Some advantages of supported catalysts are that they can readily be removed from the product by filtration, and reused. Thus, products can be prepared uncontaminated by catalyst residues; catalyst residues are a prime source of undesirable color in polymers. Removal of the catalyst by filtration will render the "living" end of the polymer more stable, of major benefit in further processing.

In the examples, experiments and comparative experiments which follow, temperatures are in degrees Celsius. Examples 4A, 10A, 23A and 26–28 provide representative descriptions of the preparation of supported GTP initiators. Experiments C-1 to C-7 provide representative descriptions of the preparation of supported GTP catalysts. Examples 1 to 25 provide representative descriptions of the preparation of "living" polymers using either supported initiators or supported catalysts. Comparative Experiments 1 to 5 provide descriptions of polymerization processes which are similar to but outside the invention. Examples 29–31 provide descriptions of some of the utilities of products prepared by the process of the invention. Following is a discussion which is applicable to the examples, experiments and comparative experiments.

EXPERIMENTS

Experiment C-1 demonstrates the exchange of the chloride of a commercial crosslinked polystyrene resin containing covalently bound quaternary ammonium groups for acetate, using tetrabutylammonium acetate in an organic solvent mixture.

Experiment C-2 is similar to Experiment C-1, except that sodium acetate, rather than tetrabutylammonium acetate, was used for the anion-exchange. A potential advantage of the method of Experiment C 2 over that of Experiment C-1 is that, should any of the ion exchange reagent (sodium acetate or tetrabutylammonium acetate) remain with the resin after the washing processes, the sodium acetate would be virtually insoluble in the tetrahydrofuran (THF) used as the polymerization medium (in contrast to tetrabutylammonium acetate) and would be unlikely to produce GTP catalysis in solution.

Experiment C-3 describes a procedure for quaternization of the tertiary amino groups of the crosslinked polystyrene-grafted block copolymer of MMA and N,N-dimethylaminoethyl methacrylate, prepared by the procedure of Example 4B. The quaternary ammonium bromide is then exchanged for m-chlorobenzoate using sodium m-chlorobenzoate.

Experiment C-4 is like Experiment C-3, except that sodium acetate is used for the ion exchange. In Experiments C-3 and C-4, a support containing acrylic-type polymer (in addition to polystyrene) is used.

Experiment C-5 demonstrates the preparation of a supported cyanide catalyst by ion exchange of the commercial resin of Experiments C-1 and C-2.

Experiment C-6(A) demonstrates another preparation of a supported catalyst in which the anion (an aryl acetate) is bound covalently to the support. Thorough extraction and further washings in Experiment C-6(B) appear to have eliminated unbound base.

Experiment C-7 is similar to Experiment C-2, except that m-chlorobenzoate was used instead of acetate.

Examples 1–3 demonstrate the use of the solid initiator of Example 26 for polymerization of methyl methacrylate (MMA) neat and in solution, and for polymerization of neat N,N-dimethylaminoethyl methacrylate.

Example 4 shows the preparation of solid initiator similar to that of Example 26, but with a lower loading. The resulting initiator is used for the sequential polymerization of MMA followed by N,N-diethyl-aminoethyl methacrylate to give a block copolymer grafted to the support. The more polar monomer units (diethylaminoethyl methacrylate) being located distal to the support should provide a useful substrate for selective binding with biomaterials such as DNA for performing separations.

Examples 5(A) and (B) show the polymerization of acrylonitrile (AN) with solid initiator of Example 4A both at −50° and at room temperature. At −50° conversion of monomer was quantitative and no ungrafted polyAN was detected. On the other hand, polymerization at room temperature led to incomplete conversion and formation of ungrafted polymer (due to chain transfer). Thus, the low temperature process eliminates chain transfer as well as chain termination processes.

Example 6 demonstrates GTP of N,N-dimethylacrylamide to give a low yield of grafted polymer using the solid initiator of Example 4A and bifluoride catalyst.

Example 7 shows low conversion of phenyl vinyl sulfone to grafted polymer using the solid initiator of Example 4A and bifluoride ion.

Example 8, using MMA as monomer, demonstrates the initiation of GTP with the polysiloxane of Example 27 and removal of the polymer from the support, some of which was retained by the poly(methyl methacrylate), PMMA.

Example 9 shows use of the initiator silica of Example 28 to polymerize MMA to give a modest yield of PMMA which is slightly more isotactic than normal PMMA prepared by GTP in homogeneous solution with the same catalyst and at the same temperature.

Example 10 shows an alternative preparation of silyl ketene acetal-containing crosslinked polystyrene and its use in polymerizing MMA. Although the initiator of Example 10A has a much shorter "spacer" than the initiator of Example 26, it nevertheless functions quite well as an initiator.

Example 11 illustrates the process of grafting a monomer from the gas phase onto a surface which has been functionalized with a silyl ketene acetal and treated with a catalyst.

Example 12, using MMA as the monomer, illustrates the use of a polymer-supported GTP chain transfer agent, with conventional GTP conditions, wherein during the polymerization there is "in situ" production of supported initiator, to produce grafting of the PMMA onto the support. As the experiment was run, about 37% of the PMMA was grafted to the chain transfer support, and 63% of the PMMA was formed in solution by direct initiation by silyl ketene acetal.

Example 13 illustrates the process of grafting acrylonitrile from the gas phase onto a surface which has been functionalized with a silyl ketene acetal and doped with catalyst.

Example 14 illustrates the process of grafting N-ethyl maleimide from the gas phase onto a surface which has been functionalized with a silyl ketene acetal and doped with catalyst.

Example 15, using MMA as the monomer, demonstrates the use of the acetate catalyst of Experiment C-1 in GTP, producing polymer with molecular weight control of the major portion of polymer, but with a high molecular weight fraction (which appears to be characteristic of most of the examples of supported catalysis of GTP). The stereochemistry of the PMMA is not much different from that of PMMA prepared by GTP with homogeneous catalysis.

Example 16 is similar to Example 15, except that the supported acetate of Experiment C-2 was used. The results are similar. In addition, to show that a solubilized catalyst was not involved, part of the reaction mixture was filtered, and the filtrate used as a catalyst-source for further GTP. Some polymer did form slowly during 18 h. This polymer showed no indication of control of $M_n$ by the initiator, so it was probably not formed by a normal GTP process. The observed "grafting" of the GTP polymer onto the catalyst resin occurred not only in the case of the acetate catalyst of this example, but also with the cyanide catalyst used in other examples. No grafting of PMMA was observed when the acrylic-styrene supports of Experiments C-3 and C-4 were used to catalyze GTP. These last supports would not be expected to contain any reactive chloromethyl groups after having been subjected to GTP in their preparation.

Example 17 shows the reuse of recovered catalyst. In reuse, the rate is extremely slow, but the amount of catalyst used is very small, since in its first utilization, it became grafted with PMMA which caused great dilution of the active sites, if not steric hindrance. Nevertheless, there is still good control of $M_n$, even during the prolonged reaction period, and the high molecular weight fraction, which is characteristic of this supported catalyst, can be seen to be formed early in the process, and can be seen to be less "living" (or less active) than the "living", controlled $M_n$ fraction.

Example 18 shows the use of polymer-supported cyanide catalyst prepared from lightly crosslinked polystyrene in GTP in which the proportion of high molecular weight fraction of PMMA is greater than in the case of the supported acetate catalyst. Some livingness is demonstrated by waiting 1 h before adding another monomer, leading to partial formation of block copolymer. Interestingly, it is the high molecular weight fraction which grows upon addition of the second monomer.

Example 19, using MMA as the monomer, demonstrates the catalysis of GTP with m-chlorobenzoate supported on an acrylic-styrenic support (made by GTP). The activity of the catalyst is low, and polymerization is quite slow, but the low $M_n$ fraction shows good control of molecular weight by the initiator and, as in Example 17, the high molecular weight fraction forms early and then becomes overwhelmed by the long-lived low molecular weight fraction.

Example 20 is like Example 19, except that ethyl acrylate (EA) was used instead of MMA. The EA polymerizes faster than the MMA but is shorter lived and less well controlled.

Example 21 is similar to Example 19, but uses an acrylic-styrenic acetate catalyst. Conversion is slower than with the m-chlorobenzoate analog. More of the high molecular weight fraction was isolated in the precipitated polymer.

Example 22 demonstrates the use of a supported m-chlorobenzoate catalyst to prepare a block copolymer of MMA and dimethylaminoethyl methacrylate. Most of the second block did not polymerize.

Example 23 shows the preparation of a polymer-supported silyl ketene acetal which differs from that of Example 10 only in having one less carbon atom in the spacer group, and its use to initiate polymerization of MMA.

Example 24 shows how the normally rather broad molecular weight distributions resulting from polymerization of MMA with supported catalysts can be improved by the addition of some acetonitrile to the solvent. The acetonitrile does not become incorporated into the polymer to an appreciable extent. The acetonitrile appears to slow down the polymerization somewhat.

Example 25 shows the effectiveness in Group Transfer Polymerization of an acetate catalyst which is obtained by ion exchange (using sodium acetate) of macroreticular, 20% divinylbenzene-crosslinked polystyrene ("Amberlyst" A27) containing quaternary groups.

Example 26 demonstrates a convenient 1-step synthesis of a silyl ketene acetal grafted to insoluble crosslinked polystyrene beads starting with commercially available chloromethylated crosslinked polystyrene beads. A disadvantage of this route is that the alkylation of the bis(silyl ketene acetal) does not proceed to completion, and as a result, there are residual chloromethyl groups which seem to slowly consume catalyst when carrying out GTP, so that a slow feed of catalyst is generally required. An alternative synthesis of silyl ketene acetal-grafted polystyrene beads which avoids this problem is illustrated in Examples 10A and 23A.

Example 27 illustrates insolubilization of the support (a polysiloxane) by means of hydrosilation of a polyfunctional methacrylate such that the resulting silyl ketene acetal groups are bound to the support through silicon. Thus, aside from the different chemical nature of the backbone relative to the experiments with cross-linked polystyrene, the nature of the attachment of initiator to support is such that propagation will always occur at the polysiloxane surface and the "dead" end of the growing polymer will be distal to the support, as opposed to those examples wherein the "living" end is distal. Any deaths of the "living" polymer will result in disconnection of the grafted polymer from the support.

Example 28 shows the preparation of chlorinated silica and its conversion to silyl ketene acetal initiator.

Examples 29-31 illustrate the use of the subject invention to chemically modify the surfaces of solids to promote binding, retention, and hybridization of DNA. Three tests of surface reactivity before and after graft modification are demonstrated.

Nucleic acid hybridization tests, also referred to as DNA or RNA probe tests, are useful in detecting and identifying genetic information encoded in cellular DNA or RNA. Hybridization tests are thus providing important new diagnostic capability—yielding information on the genetic basis and susceptibility to disease as well as on the causative organisms of disease. For example, hybridization testing has established relationships between viral infections and cancer. Prenatal diagnosis of genetic disease and detection of carriers have been demonstrated. These and other applications have recently been reviewed (J. B. Lowe, "Clinical applications of gene probes in human disease, malignancy and infection", Clin. Chim. Acta., 157, 1 (1986)).

Although the solid supports and grafting conditions described herein have not been optimized for either the preparation of reagents or use in clinical probe assays, Examples 29-31 clearly illustrate that the chemical properties of solids can be usefully altered by GTP grafting to provide appropriate molecular interactions needed in probe assays, such as the binding and retention of DNA from solution and hybridization with probe.

Comparative Experiment 1 demonstrates the preparation of a supported carboxylate in which the anion is covalently bound to the support and tetrabutylammonium is the counter ion.

Comparative Experiment 2 is a control experiment to determine whether soluble catalyst is obtained by extraction of the supported acetate catalyst of Experiment C 2 with THF (Part A) or with THF and silyl ketene acetal (Part B). Although the filtered extracts very slowly lead to some polymer formation, the $M_n$ is not controlled by the silyl ketene acetal, and no polymer was observed during the time period in which the supported catalyst produces complete polymerization of MMA.

Comparative Experiment 3 shows the use of catalyst in which the aryl acetate is covalently bound to the support and the counter ion is tetrabutylammonium. An induction period is observed, followed by rapid polymerization, giving good molecular weight control and no distinct high molecular weight fraction.

Comparative Experiment 4 is a control experiment which shows that the catalyst used in Comparative Experiment 3 functions by reacting with initiator to generate a soluble catalyst which is the active catalyst for the polymerization.

Comparative Experiment 5 is a control experiment which shows that a supported catalyst which is operable with a soluble initiator, and a supported initiator which is operable with a soluble catalyst, are not operable with each other in causing polymerization of MMA, because two reactants on separate supports cannot come into the intimate contact needed for reaction. This is evidence that a soluble catalyst does not come off of the support.

EXPERIMENTS

Experiment C-1 - Preparation of Insoluble Crosslinked Polystyrene-supported Tributylmethylammonium Acetate - Tetrabutylammonium Acetate Procedure A small chromatography column was packed with 2 g of tributylmethylammonium chloride bound on polystyrene (200-400 mesh) crosslinked with 1% divinylbenzene (Fluka Co., activity about 0.85 meq/g, catalog 90806), and a solution of 6 g of tetrabutylammonium acetate in 50 mL of 3:1 tetrahydrofuran (THF)-methanol was slowly passed over the column during about 2.5 h. The resin was then washed well sequentially with methanol, water, and THF. The product was then extracted overnight with THF in a Soxhlet apparatus. After drying in vacuo at room temperature, the IR spectrum of the product (KBr) showed absorption at 1580 and 1375 cm$^{-1}$ characteristic of carboxylate C=O, and, in addition, a weak ester C=O at 1740 cm$^{-1}$ probably due to the reaction of acetate with residual chloromethyl groups present in the commercial sample of resin. Anal. found: N 0.86, Cl 0.90% corresponding to 0.6 meq/g of N and 0.2 meq/g of Cl. Infrared: 1740 cm$^{-1}$ (w, ester C=O), 1580 cm$^{-1}$ (RCOO$^-$).

Experiment C-2 - Preparation of Insoluble, Crosslinked Polystyrene-supported Methyltributylammonium Acetate - Sodium Acetate Procedure A small chromatography column was packed with 3 g of the same commercial tributylmethyl-ammonium chloride supported on crosslinked polystyrene which was used in Experiment C-1. A saturated solution of sodium acetate in 400 mL of 50% aqueous methanol was slowly passed over the resin. The resin was then washed successively with 500 mL of 50% aqueous methanol, 1 L of water, 1 L of methanol, 1 L of anhydrous tetrahydrofuran and dried in vacuo at room temperature. Anal. found: N 1.19, Cl 0.35% corresponding to 0.85 meq/g of N and 0.1 meq/g of Cl. Infrared analysis: 1740 cm$^{-1}$ (ester C=O), 1580 and 1360 cm$^{-1}$ (RCOO$^-$).

Experiment C-3 - Preparation of Insoluble, Crosslinked Polystyrene-grafted Poly(Methyl Methacrylate-b-β-Dimethylaminoethyl Methacrylate)-Supported Ethyldimethylbenzylammonium m-Chlorobenzoate A suspension of 1.5 g of polystyrene beads crosslinked with 1% divinylbenzene and grafted by Group Transfer Polymerization with a block copolymer of methyl methacrylate and β-dimethylaminoethyl methacrylate (as described in Example 4B) in 10 mL of anhydrous propylene carbonate was treated with 10 mL of benzyl bromide and stirred at 110° for 3 days. The resin was collected by filtration and washed with tetrahydrofuran, water, and methanol. The product was dried and then extracted overnight in a Soxhlet apparatus with tetrahydrofuran over metallic sodium. Anal. found: N 0.84, Br 6.10% corresponding to 0.6 meq/g of N and 0.76 meq/g of Br. The analysis is consistent with the desired quaternary ammonium bromide. The product was placed in a chromatography column, and 400 mL of a solution of sodium m-chlorobenzoate in 50% aqueous methanol (prepared by dissolving 47 g of m-chlorobenzoic acid in a solution of 11.6 g of sodium hydroxide in 200 mL of water followed by dilution to 400 mL with methanol) was slowly passed over the resin. The product was washed successively with 500 mL of 50% aqueous methanol, 500 mL of water, 500 mL of methanol, and 500 mL of tetrahydrofuran. The product was extracted overnight in a Soxhlet apparatus with tetrahydrofuran over metallic sodium to give the insoluble quaternary ammonium m-chlorobenzoate. Anal. found: N 0.90, Cl 2.46% corresponding to 0.6 meq/g of N and 0.7 meq/g of Cl.

Experiment C-4 - Preparation of Insoluble, Crosslinked Polystyrene-grafted Poly(Methyl Methacrylate-b-$\beta$-Dimethylaminoethyl Methacrylate)-Supported Ethyldimethylbenzylammonium Acetate The procedure of Experiment C-3 was followed using sodium acetate instead of sodium m-chlorobenzoate for the anion-exchange. Anal. found: N 0.84, Br 2.48% corresponding to 0.6 meq/g of N and 0.3 meq/g of Br. Thus, only about 50% of the bromide ion was exchanged for acetate ion.

Experiment C-5 - Preparation of Insoluble, Crosslinked Polystyrene-Supported Tributylmethyl-ammonium Cyanide The commercial polystyrene-supported tributylmethylammonium chloride used in Experiment C-1 (6 g) was placed in a chromatography column and treated with a solution of 40 g of potassium cyanide in 50% aqueous methanol. The resin was then washed with 800 mL portions of 50% aqueous methanol, water, and tetrahydrofuran. The resin was then extracted in a Soxhlet apparatus for 20 h with tetrahydrofuran over sodium, and dried to give polystyrene-supported tributylmethylammonium cyanide. Anal. found: N 1.85%, Cl 0.42% which corresponds to 1.3 meq/g of N and 0.1 meq/g of residual Cl.

Experiment C-6 - Preparation of Crosslinked Polystyrene-Supported Tetrabutylammonium Phenylacetate A. A small chromatography column was packed with 3 g of crosslinked polystyrene (crosslinked with 1% divinylbenzene) bound phenylacetic acid (prepared by the procedure of Darling and Frechet, *J. Org. Chem.*, 1986, 51, 2270), and a solution of 50 mL of tetrabutylammonium hydroxide (1M in methanol) in 100 mL of tetrahydrofuran was slowly passed over the resin. The product was washed with tetrahydrofuran, methanol, and tetrahydrofuran, and extracted in a Soxhlet apparatus with tetrahydrofuran over sodium. The resin was dried in vacuo. Anal. found: N 2.60% which corresponds to 1.86 meq/g of tetrabutylammonium.

B. One half of the supported catalyst of Part A was placed in a chromatography column and washed with water, methanol, and tetrahydrofuran and dried at 60° and 0.1 Torr. Anal. found: N 2.44% which corresponds to 1.74 meq/g of tetrabutylammonium.

Experiment C-7 - Preparation of Insoluble, Crosslinked Polystyrene-Supported Tributylmethylammonium m-chlorobenzoate A 5-gram sample of commercial polystyrene-supported tributylmethylammonium chloride (activity approximately 0.85 meq/g of Cl, as described in Experiment C-1) was placed in a chromatography column, and 800 mL of a solution of sodium m-chlorobenzoate in 50% aqueous methanol (prepared by dissolving 94 g of m-chlorobenzoic acid in a solution of 23.2 g of sodium hydroxide in 400 mL of water followed by dilution to 800 mL with methanol) was slowly passed over the resin. The product was washed successively with 1 L of 50% aqueous methanol, 1 L of water, 1 L of methanol, and 1 L of tetrahydrofuran. The product was then extracted in a Soxhlet apparatus with tetrahydrofuran over sodium. The product was then stirred for 2 h with 110 mL of tetrahydrofuran and 2 mL of 1-methoxy-1-trimethylsiloxy-2-methyl-1-propene. The 2 mL of methanol was added, and after 10 min the product was collected by filtration, washed with tetrahydrofuran, and extracted in a Soxhlet apparatus with tetrahydrofuran over sodium.

Infrared analysis of the product showed absorption at 1555 and 1360 cm$^{-1}$ characteristic of COO$^{31}$, and weak absorption at 1720 cm$^{-1}$ (ester C=O). Anal. found N 1.03%, Cl 2 74% which corresponds to 0.7 meq/g of N and 0.77 meq/g of Cl.

EXAMPLES

Example 1 - Initiation of Polymerization of Neat Methyl Methacrylate with Crosslinked Polystyrene with Pendant Silyl Ketene Acetal Functions To a stirred mixture of 1 g of the product of Example 26 and 15 mL of methyl methacrylate (MMA) was added dropwise 0.5 mL of a 0.1M solution of tetrabutylammonium m-chlorobenzoate in tetrahydrofuran (THF) during 15 min. The reaction temperature slowly rose to 37°, and after 3 h, the liquid methyl methacrylate had been completely absorbed by the polystyrene beads by swelling The mixture was diluted with THF and filtered. The filter cake was repeatedly extracted with THF, filtered, and dried in vacuo to give 4.23 g of solid polymer The infrared spectrum of the product showed absorption characteristic of poly(methyl methacrylate) PMMA and polystyrene, with the former predominating.

Example 2 - Initiation of Polymerization of Methyl Methacrylate in THF Solution with Crosslinked Polystyrene with Pendant Silyl Ketene Acetal Functions To a stirred slurry of 2 g of the silyl ketene acetal-grafted crosslinked polystyrene beads of Example 26 and 2.16 mL (20 mmol) of MMA in 20 mL of THF was added dropwise during 30 min. 0.3 mL of 0.1M tetrabutylammonium m-chlorobenzoate in THF. A slow exotherm caused the temperature to rise from 25° to 31° during the addition of catalyst. The temperature slowly fell during 3 h. NMR-analysis of a small sample of the supernate showed the presence of only a trace of MMA. The product was filtered and washed with THF. Evaporation of the filtrate gave a trace of PMMA. After further extraction of the polymeric beads with THF during 18 h, filtration and drying gave 4 g of polystyrene beads grafted with PMMA. Infrared analysis of the product showed absorption characteristic of PMMA and of polystyrene.

Example 3 - Initiation of Polymerization of Neat N,N-Dimethylaminoethyl Methacrylate with Crosslinked Polystyrene with Fendant Silyl Ketene Acetal Functions To a stirred slurry of 1 g of the silyl ketene acetal-grafted crosslinked polystyrene beads of Example 26 in 15 mL of N,N-dimethylaminoethyl methacrylate was added 0.5 mL of 0.1M tetrabutylammonium bibenzoate in THF. The temperature increased 1.7°. After 1 h, the mixture was diluted with THF and filtered. The filter cake was washed several times with THF, and then extracted 18 h with THF, filtered and dried to give 1.55 g of polystyrene beads grafted with poly(N,N-dimethylaminoethyl methacrylate). Infrared analysis showed strong absorption at 1728 cm$^{-1}$ characteristic of unconjugated ester, in addition to absorption characteristic of polystyrene Example 4

A. Preparation of Crosslinked Polystyrene Beads with Pendant Silyl Ketene Acetal Functions Using the same general procedure as Example 26, 10 g of chloromethylated polystyrene beads crosslinked with 1% divinylbenzene (Bio-Rad Laboratories) containing only 1 36 meq Cl/g, was reacted with 10 4 g of 1,2-bis(1-trimethylsiloxy-2-methyl-1-propenoxy)ethane and 1.25 g of zinc chloride in 40 mL of dichloromethane. The purified product showed strong infrared absorption at 1705 cm$^{-1}$ characteristic of a silyl ketene acetal. Elemental analysis showed 1 86% Si and 1.19% Cl corresponding to 0.66 meq/g of Si and 0.33 meq/g of residual Cl.

B. Initiation of Polymerization of Methyl Methacrylate and N,N-Dimethylaminoethyl Methacrylate to Form a Block Copolymer Grafted to Crosslinked Polystyrene To a stirred slurry of 2 g of silyl ketene acetal-grafted polystyrene beads prepared in Part A and 1 g of MMA (10 mmol) in 20 mL of THF was added dropwise during 1 h 0.3 mL of 0.1M tetrabutylammonium m-chlorobenzoate. After 30 min, a small sample of supernate was removed for NMR analysis which showed approximately 2% of unreacted monomer. Then 0.84 mL (5 mmol) of N,N-dimethylaminoethyl methacrylate was added as catalyst addition was continued. With both monomers, a temperature rise of about 1° was observed. Thirty minutes after catalyst addition was complete, a sample was removed for NMR analysis which showed about 2% residual monomer. The product was washed with THF and filtered. After extracting with THF in a Soxhlet extractor for 18 h, the product was dried to give 3.16 g of crosslinked polystyrene beads with grafted block copolymer of PMMA and poly(N,N-dimethylaminoethyl methacrylate). Elemental analysis showed 1.29% N corresponding to 0.92 meq/g of N,N-dimethylaminoethyl methacrylate units in the block copolymer. The infrared spectrum of the product shows absorption at 1730 cm$^{-1}$ (ester C=O) and 2770 cm$^{-1}$ (N-methyl).

Example 5 - Initiation of Polymerization of Acrylonitrile with Silyl Ketene Acetal Grafted on Crosslinked Polystyrene A To a stirred slurry of 1 g of the crosslinked polystyrene initiator beads of Example 4A and 0.66 mL (10 mmol) of acrylonitrile (purified by passage over a column of alumina) in 10 mL of N,N-dimethylformamide (DMF) and 2 mL of THF cooled to −50° was added dropwise during 30 min 2 mL of 0.01M tris(dimethylamino)sulfonium bifluoride in DMF. A small sample of the supernate was removed for analysis. NMR showed no residual monomer. The product was filtered and washed with DMF. The filtrate was concentrated under reduced pressure to 0.25 its original volume. Addition to water gave no precipitation of dissolved polymer. The product was extracted with dimethyl sulfoxide, and finally extracted with THF in a Soxhlet extractor for 18 h to give, after drying, 1.45 g of polystyrene grafted with poly(acrylonitrile). Infrared analysis shows the presence of considerable nitrile (strong absorption at 2240 cm$^{-1}$) Elemental analysis showed 78.94% C, 7.18% H, 8.32% N, corresponding to 5.9 meq/g of acrylonitrile units.

B. In a similar experiment performed at room temperature, residual monomer was detected in the supernate, and 0.14 g of poly(acrylonitrile) was isolated from the supernate. There was obtained 1.19 g of polystyrene containing grafted poly(acrylonitrile). Elemental analysis showed 6.07% N, corresponding to 4.3 meq/g of acrylonitrile units. The intensity of the 2240 cm$^{-1}$ absorption (CN) in the infrared spectrum of the product was less intense (relative to polystyrene peaks) than in the product prepared at −50°.

Example 6 - Initiation of Polymerization of N,N-Dimethylacrylamide with Silyl Ketene Acetal Grafted on Crosslinked Polystyrene To a stirred slurry of 1 g of the crosslinked polystyrene initiator beads of Example 4A and 1 mL (10 mmol) of N,N-dimethylacrylamide in 10 mL of THF was added dropwise during 1 h 0.5 mL of 0.1M tris(dimethylamino)sulfonium bifluoride in propylene carbonate. Less than 1° rise in temperature was observed After stirring overnight, the supernate was sampled and found by infrared analysis to contain residual monomer. The polystyrene beads were isolated by filtration, washed with THF, and extracted for 18 h with THF in a Soxhlet apparatus. There was obtained, after drying, 1 g of polystyrene grafted with poly N,N-dimethylacrylamide. Infrared analysis of the product showed ester C=O absorption at 1730 cm$^{-1}$ and amide absorption at 1645 cm$^{-1}$. Elemental analysis showed 1.02% N corresponding to 0.73 meq/g of N,N-dimethylacrylamide units.

Example 7 - Initiation of Polymerization of Phenyl Vinyl Sulfone with Silyl Ketene Acetal Grafted on Crosslinked Polystyrene To a stirred slurry of 1 g of the crosslinked polystyrene initiator beads of Example 4A and 1 g of phenyl vinyl sulfone in 10 mL of anhydrous pyridine was added dropwise during 30 min 0.1 mL of 0.1M tris(dimethylamino)sulfonium bifluoride in acetonitrile. During the first 10 min of catalyst addition, the temperature rose more than 1° and then slowly fell. Analysis of the supernate by NMR showed residual monomer. The product was extracted with pyridine and with THF. Finally, the product was extracted for 18 h in a Soxhlet apparatus to give, after drying, 1.03 g of polystyrene grafted with poly(phenyl vinyl sulfone). Infrared analysis of the product showed absorption at 1305 and 1145 cm$^{-1}$ (weak) characteristic of the sulfone group. Elemental analysis found 1.75% S, corresponding to 0.54 meq/g of phenyl vinyl sulfone units.

Example 8 - Initiation of Polymerization of Methyl Methacrylate with a Crosslinked Polydimethylsiloxane Resin Containing Silyl Ketene Acetal Groups To a stirred slurry in 40 mL of THF of 0.5 g of crosslinked polydimethylsiloxane containing silyl ketene acetal functionality from Example 27A and 20 µL of 1M tris(dimethylamino)sulfonium bifluoride in acetonitrile was added 10.8 ml of MMA at a rate to maintain a temperature of 41°. Before all of the MMA had been added, the temperature gradually fell. A small temperature rise was obtained by addition of two more 10 µL portions of the IM catalyst solution. When the temperature had fallen to room temperature, the reaction mixture was poured into aqueous methanol in a blender to give after filtration 4.3 g of solid polymer. The product was stirred for 1.5 h with 40 mL of THF and 6 mL of 10% methanolic hydrochloric acid and filtered through Celite TM. The polymeric product was precipitated from the filtrate with aqueous methanol in a blender. The product was then precipitated from dichloromethane with hexane and from THF with aqueous methanol to give 3.3 g of polymer. NMR analysis showed 25 MMA units per dimethylsilyl unit. GPC showed $M_n$ 90,400, $M_2$ 946,000, D=10.46. NMR analysis showed that the polymer was 6.6% isotactic, 38.5% heterotactic, and 54.9% syndiotactic.

Example 9 - Initiation of Polymerization of Methyl Methacrylate with Silica-Containing Silyl Ketene Acetal Functions To a stirred slurry of 1.5 g of silica gel containing pendant silyl ketene acetal groups from Example 28 in 30 mL of THF and 5.4 mL (50 mmol) of MMA was added portionwise 1M tris(dimethylamino)sulfonium bifluoride in acetonitrile until there was no longer a discernible increase in temperature. A total of 0.4 mL of the catalyst solution was required, and a total temperature increase of about 2° occurred. After stirring for 3 h, the mixture was filtered, and the filter cake was washed with anhydrous THF. Evaporation of the filtrate gave 1.3 g of PMMA. The filter cake (silica) weighed 1.6 g. $^1$H-NMR analysis showed that the PMMA was 52.3% syndiotactic, 40.7% heterotactic, and 7% isotactic

Example 10

A. Preparation of Crosslinked Polystyrene Beads with Pendant Silyl Ketene Acetal Functions To a stirred mixture of 5 g of crosslinked polystyrene beads containing 4 meq/g of hydroxyethyl groups (prepared as indicated in the equation using essentially the procedure of Darling and Frechet, *J. Org. Chem.*, 51, 2270 (1986))

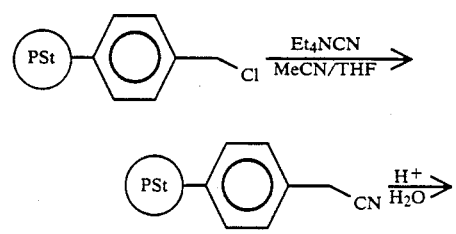

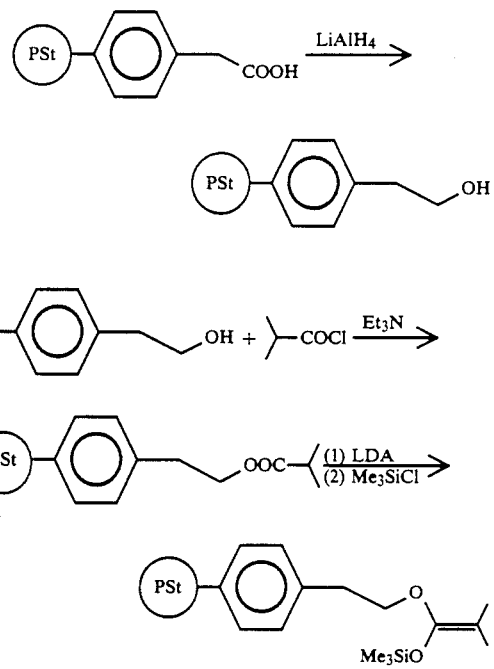

and 5.6 mL (40 mmol) of triethylamine in 75 mL of dichloromethane was added 4.2 mL (40 mmol) of isobutyryl chloride. The mixture was stirred for 18 h and filtered, and the filter cake was washed with dichloromethane, water, and then THF. The product was extracted with THF in a Soxhlet apparatus 18 h. The infrared spectrum of the product shows absorption characteristic of saturated ester C=O at 1733 cm$^{-1}$ with no indication of any residual hydroxyl functionality. The resulting isobutyrate (5 g) was added to a solution of lithium diisopropylamide (cooled to 0°) prepared from 5.6 mL (40 mmol) of diisopropylamine and 40 mmol of 1.6M butyl lithium/hexane in 100 mL of THF. After stirring for 2 h, the mixture was cooled to −78° and treated with 5.7 mL (45 mmol) of chlorotrimethylsilane. After 1 h at −78°, the mixture was stirred 2 h at 0°. The product was filtered under argon and washed with THF. The product was extracted in a Soxhlet apparatus with THF and dried in vacuo to give 4.43 g of crosslinked polystyrene beads containing silyl ketene acetal functional groups. The infrared spectrum of the product (KBr wafer) showed strong absorption at 1702 cm$^{-1}$ characteristic of a silyl ketene acetal group. In addition there was absorption at 1730 cm$^{-1}$ characteristic of ester C=O.

B. Initiation of Polymerization of Methyl Methacrylate with Crosslinked Polystyrene Beads with Pendant Silyl Ketene Acetal Functions To a stirred mixture of 1 g of crosslinked polystyrene beads containing silyl ketene acetal functions from Part A and 2.16 mL (20 mmol) of MMA in 15 mL of THF was added dropwise during 20 min 0.4 mL of 0.1M tetrabutylammonium m-chlorobenzoate in THF. During this period, the temperature rose 13° and then began to fall before the last of the catalyst solution had been added. After stirring for 1 h, the mixture was quenched with 1 mL of methanol, and a sample of the supernate was removed for NMR analysis which showed no residual MMA. The product was collected by filtration and washed with THF. Evaporation of the filtrate gave no polymeric residue, indicating that all of the PMMA was grafted to the polystyrene beads. The product was extracted with THF in a Soxhlet apparatus and dried to give 2.93 g of polystyrene beads grafted with PMMA.

Example 11 - Initiation of Polymerization of Gaseous Methyl Methacrylate with Crosslinked Polystyrene with Pendant Silyl Ketene Acetal Groups Pretreated with Tetrabutylammonium m-Chlorobenzoate To 15 mL of THF was added 0.16 mL of 0.38M tetrabutylammonium m-chlorobenzoate in THF and 0.2 g of crosslinked polystyrene beads containing silyl ketene acetal groups from Example 10A. After stirring for 10 min, the polymer was removed by filtration and allowed to stand in a nitrogen atmosphere in a dry box for 24 h. Then 0.2 g of the polymer was placed in a small cup and placed in a closed chamber containing 2 mL of MMA in a second small cup. After 24 h, the weight of the polymer had increased to 0.5 g due to initiation of polymerization of MMA which had migrated through the gas phase to the silyl ketene acetal-containing crosslinked polystyrene beads. Extraction of 200 mg of the polystyrene beads grafted with PMMA for 3 days with THF produced only 0.8 mg (0.4%) of THF-soluble material, which confirms that virtually all of the PMMA is grafted to the insoluble polystyrene. IR analysis of the polystyrene beads after extraction with THF showed the presence cf poly(methyl methacrylate) and a lesser amount of polystyrene.

Example 12 - Chain Transfer to Crosslinked Polystyrene Beads with Pendant Benzyl Cyanide in Polymerization of Methyl Methacrylate To a stirred mixture of 1 g of crosslinked polystyrene containing pendant cyanomethyl groups (activity 4.0 meq/g of CN) prepared by the procedure used in Example 10A, 30 mL of THF, 0.2 mL (1 mmol) of 1-methoxy-1-trimethylsiloxy-2-methyl-1-propene, and 1 mL of methyl methacrylate was added 30 μL of tetrabutylammonium m-chlorobenzoate (0.4 M in THF). Then a solution of 15 μL of tetrabutylammonium m-chlorobenzoate (0.4 M in THF) in 4.4 mL of MMA was added during a period of 45 min. Exothermic polymerization was observed. When the exotherm was over, a sample of the supernate was removed for analysis. $^1$H NMR showed that both monomer and PMMA were present in the solution (8.5% methyl methacrylate, 91.5% PMMA). The polystyrene beads were removed by filtration and extracted in a Soxhlet apparatus with THF. After drying, 2.6 g of polystyrene beads were obtained. IR analysis showed that there was much grafted PMMA on the styrene beads, and CN absorption at 2240 cm$^{-1}$ was observed. The filtrate was evaporated under reduced pressure, and the residue was precipitated from methylene chloride with hexane to give, after drying, 2.77 g of PMMA, $M_n$ 6670, $M_w$ 9180, D=1.376, with a long low, molecular weight tail.

Example 13 - Initiation of Polymerization of Gaseous Acrylonitrile with Crosslinked Polystyrene with Pendant Silyl Ketene Acetal Groups Pretreated with Tetrabutylammonium m-Chlorobenzoate The general procedure of Example 11 was followed using 50 mg of the catalyst-doped silyl ketene acetal beads and 1 mL of acrylonitrile instead of methyl methacrylate. IR analysis of the polymeric product after drying under reduced pressure showed CN absorption at 2240 cm$^{-1}$ and no remaining absorption at 1705 cm$^{-1}$. Analysis found N 2.71% corresponding to 1.9 meq/g of N.

Example 14 - Initiation of Polymerization of Gaseous N-Ethyl Maleimide with Crosslinked Polystyrene with Pendant Silyl Ketene Acetal Groups Pretreated with Tetrabutylammonium m-Chlorobenzoate The general procedure of Example 11 was followed using 50 mg of the catalyst-doped silyl ketene acetal beads and 1 g of N-ethyl maleimide dissolved in a minimum of 1-chloronaphthalene. IR analysis of the product after drying under reduced pressure showed weak imide C=O absorption at 1770 cm$^{-1}$. Analysis found: N 0.46% corresponding to 0 3 meq/g of N.

Example 15 - Catalysis of Polymerization of Methyl Methacrylate with Polymer-Supported Acetate Catalyst of Experiment C-1

To a stirred mixture of 30 mL of tetrahydrofuran, 0.1 g of the insoluble polymer-supported acetate catalyst of Experiment C-1, and 5.4 mL (50 mmol) of methyl methacrylate (purified by passage over a column of neutral alumina under argon) was added 0.2 mL (1 mmol) of 1-methoxy-1-trimethylsiloxy-2-methyl-1-propene. During 1 min, the temperature of the reaction mixture rose from 24.8° to 46.6°, reaching a maximum of 54.4° in about 2.5 min. A sample of the supernate was removed for analysis by $^1$H-NMR, which showed that there was no residual monomer. After removal of the catalyst by filtration, the poly(methyl methacrylate), PMMA, was precipitated in hexane. Gel permeatior chromatograhic (GPC) analysis of the PMMA showed the polymer to be bimodal in molecular weight with $M_n$ 4660, $M_w$ 27,400, D=5.9 (theory $M_n$ 5100). Approximately 80% of the polymer consisted of a narrow molecular weight distribution peak with peak molecular weight about 3200, and 20% consisted of a high molecular weight shoulder with peak molecular weight about 56,000. $^1$H NMR analysis of the polymer showed the tacticity to be 4.2% isotactic, 38.5% heterotactic and 57.3% syndiotactic.

Example 16 - Catalysis of Polymerization of Methyl Methacrylate with Polymer-Supported Acetate Catalyst of Experiment C-2

To a mixture of 30 mL of tetrahydrofuran, 0.1 g of polymer-supported acetate catalyst of Experiment C-2, and 5.4 mL (50 mmol) of methyl methacrylate (purified as in Example 15) was added 0.2 mL (1 mmol) of 1-methoxy-1-trimethylsiloxy-2-methyl-1-propene. The temperature of the reaction mixture rose from 23.4° to 49.6° during 3 minutes. A small sample of the supernate was removed for analysis. $^1$H NMR showed that there was no residual monomer. GPC analysis showed a bimodal molecular weight distribution similar in appearance to that of Example 8, with $M_n$ 4040, $M_w$ 30,400, D=7.5. Approximately 80% of the polymer had a fairly narrow molecular weight peak with $M_p$ about 4000, while 20% appeared as a high molecular weight shoulder with $M_p$ 50,000. Approximately 15 mL of supernate from the reaction mixture was filtered under argon through a fritted glass disc (to prevent passage of any supported catalyst) into a second flask containing 20 mL of tetrahydrofuran and 5.4 mL of methyl methacrylate. Addition of 0.2 mL of 1-methoxy-1-trimethylsiloxy-2-methyl-1-propene gave no apparent exothermic reaction. After 18 h, a sample removed from the second flask was analyzed by $^1$H NMR which showed much residual monomer, approximately equal quantities of monomer and PMMA. Precipitation of the polymer from the second flask with aqueous methanol gave 2 g of PMMA. GPC showed $M_n$ 13,400, $M_w$ 84,400, D=6.27. The molecular weight distribution was bimodal, with about 30% of the polymer having $M_p$ 5000, and 70% having $M_p$ 100,000. Thus, after removal of the supported catalyst there was some very slow formation of very high molecular weight PMMA in which $M_n$ was not controlled by the added silyl ketene acetal initiator. The supported catalyst was recovered by filtration and extracted in a Soxhlet apparatus with tetrahydrofuran to give, after drying, 0.36 g of resin. IR analysis showed the presence of PMMA, which shows that PMMA became permanently grafted to the catalyst support, perhaps through residual chloromethyl groups present in the commercial material from which the acetate catalyst was prepared.

Example 17 - The Use of Recovered Crosslinked Polystyrene-Supported Acetate Catalyst for Catalysis of Polymerization of Methyl Methacrylate A mixture of 50 mg of recovered polystyrene-supported acetate (containing grafted PMMA) from Example 16 and 30 mL of tetrahydrofuran was stirred 1 h, and then 0.2 mL (1 mmol) of 1-methoxy-1-trimethylsiloxy-2-methyl-1-propene and 5.4 mL (50 mmol) of methyl methacrylate was added. A slow rise in temperature of 1.5° occurred during 1 h. After 3 h, $^1$H NMR analysis showed 41% conversion of monomer to PMMA. GPC: $M_n$ 2880, $M_w$ 15,600, D=5.4 (theory $M_n$ 2100 for 41% conversion). Approximately 90% of the polymer showed a narrow molecular weight peak with $M_p$ 3100 while 10% was in a broad high molecular weight tail. After 24 h, analysis showed 75% conversion of monomer to PMMA. GPC: $M_n$ 3300, $M_w$ 9070, D=2.75 (theory for 75% conversion $M_n$ 3800), with the high molecular weight tail accounting for only about 4% of the polymer. $^1$H NMR analysis of the precipitated polymer shows the tacticity to be 5.5% isotactic, 38.5% heterotactic, and 56% syndiotactic, which is similar to the tacticity of PMMA prepared by Group Transfer Polymerization at 25° in homogeneous solution.

Example 18 - Catalysis of Polymerization of Methyl Methacrylate and N,N-Dimethylaminoethyl Methacrylate with Crosslinked Polystyrene-Supported Cyanide A mixture of 0.2 g of polymer-supported cyanide catalyst of Experiment C-5 and 30 mL of tetrahydrofuran was stirred for 1 h. Then 0.2 mL (1 mmol) of 1-methoxy-1-trimethylsiloxy-2-methyl-1-propene was added, and 10.8 mL (100 mmol) of methyl methacrylate was added slowly. The temperature rose 16° when 1 mL of the monomer was added. The remaining monomer was added at a rate such that the temperature remained at 35°-40°. One hour after the end of the exotherm a sample of the supernate was removed for analysis. $^1$H NMR analysis showed 94% conversion of monomer to PMMA. GPC: bimodal with $M_n$ 10,500, $M_w$ 51,600, D=4.88. About 43% of the polymer has $M_p$ 8000, and 57% has $M_p$ 43,000. Following removal of the sample, 8.5 mL (50 mmol) of N,N-dimethylamino-ethyl methacrylate was added which produced a slow increase in temperature of 1.5°. After stirring for 18 h, a sample of the supernate was removed for analysis. $^1$H NMR showed 79% polymer and 21% monomer, corresponding to polymerization of about 19% of the N,N-dimethylaminoethyl methacrylate to block copolymer. GPC: trimodal with $M_n$ 11,400, $M_w$ 60,600, D=5.3. About 2% of the polymer has $M_p$ 560, 21% has $M_p$ 12,600, and 77% has $M_p$ 45,000. The catalyst was removed by filtration and extracted in a Soxhlet apparatus with tetrahydrofuran to give 1.47 g of resin. IR shows PMMA with only a trace of polystyrene. Thus, much of the living methacrylic polymer became attached to the catalyst support resulting in a 7-fold weight increase of the catalyst. Anal. found: C 63.04, H 8.61, N 1.16% which corresponds to 0.8 meq/g of N.

Example 19 - Catalysis of Polymerization of Methyl Methacrylate with Crosslinked Polystyrene-grafted Poly(Methyl Methacrylate-b-N,N-Dimethylaminoethyl Methacrylate)-Supported Ethyldimethylbenzylammonium m-Chlorobenzoate A mixture of 30 mL of tetrahydrofuran, 0.2 g of supported m-chlorobenzoate catalyst of Experiment C-3, 0.2 mL (1 mmol) of 1-methoxy-1-trimethyl siloxy-2-methyl-1-propene, and 10.8 mL (100 mmol) of methyl methacrylate was stirred for 18 h. During the first few h, a slow rise in temperature of 1.6° was observed. Analysis by $^1$H NMR of a sample of the supernate removed from the reaction mixture after 1.5 h showed 17% conversion of methyl methacrylate to PMMA. GPC: bimodal, $M_n$ 793, $M_w$ 12,300, D=15.5, with about 80% having $M_p$ 1400, and 20% having $M_p$ 50,100 (theory for 17% conversion for the 80% low molecular weight fraction, $M_n$ 1360). A sample removed after 18 h analyzed for 38% conversion to PMMA. GPC: bimodal, $M_n$ 2820, $M_w$ 6170, D=2.19, with 97% having $M_p$ 3980, and 3% having $M_p$ about 50,000. Thus, the high molecular weight fraction formed early and rapidly in the polymerization process, while the low molecular weight fraction continued to increase in quantity and in $M_n$ steadily throughout the polymerization process indicating good "livingness" and good control of $M_n$ by the monomer:initiator ratio. The catalyst was recovered by filtration and showed no increase in weight. The PMMA was isolated from the filtrate by precipitation with aqueous methanol.

Example 20 - Catalysis of Polymerization of Ethyl Acrylate with Crosslinked Polystyrene-grafted Poly(Methyl Methacrylate-b-N,N-Dimethylaminoethyl Methacrylate)-Supported Ethyldimethylbenzylammonium m-Chlorobenzoate The procedure of Example 19 was followed using 10.8 mL (100 mmol) of ethyl acrylate instead of methyl methacrylate. A slow 3° rise in temperature was observed. Analysis of a sample of supernate removed after 1 h showed 20% conversion to poly(ethyl acrylate). GPC: bimodal, 60% with $M_n$ 2150, $M_w$ 4740, D=2.2, and 40% with $M_n$ 47,100, $M_w$ 65,800, D=1.4. A sample removed after 18 h showed no further conversion to poly(ethyl acrylate).

Example 21 - Catalysis of Polymerization of Methyl Methacrylate with Crosslinked Polystyrene-grafted Poly(Methyl Methacrylate-b-N,N-Dimethylaminoethyl Methacrylate)-Supported Ethyldimethylbenzylammonium Acetate The procedure of Example 19 was followed using 0.2 g of supported acetate catalyst of Experiment C-4 instead of supported m-chlorobenzoate catalyst of Experiment C-3. Little exothermic reaction was observed. A sample of supernate removed after 1 h showed 12% conversion of methyl methacrylate to PMMA. After 18 h the conversion was 31%. GPC: bimodal, 63% with $M_n$ 18,200, $M_w$ 65,100, D=3.57, and 37% with $M_n$ 667,000, $M_w$ 851,000, D=1.28. The recovered catalyst showed no increase in weight.

Example 22 - Catalysis of Polymerization of Methyl Methacrylate and N,N-Dimethylaminoethyl Methacrylate with Crosslinked Polystyrene-Supported m-Chlorobenzoate A mixture of 0.2 g of polymer-supported m-chlorobenzoate catalyst of Experiment C-7 and 30 mL of tetrahydrofuran was stirred for 1 h. Then 0.2 mL (1 mmol) of 1-methoxy-1-trimethylsiloxy-2-methyl-1-propene was added, and 10.8 mL (100 mmol) of methyl methacrylate was added slowly to control the very exothermic polymerization. Analysis of a sample of the mixture removed 1 h after addition of the methyl methacrylate showed (by $^1$H NMR) that 23% of the monomer remained, and the polymer had $M_n$ 8870, $M_w$ 28,100, D=3.18. Then 8.5 mL (50 mmol) of N,N-dimethylaminoethyl methacrylate was added, and the solution was stirred 18 h. Analysis of a sample of the mixture showed 41 mole percent unreacted monomer and 59 mole percent polymer. GPC: bimodal with 20% having $M_n$ 993, $M_w$ 997, D=1.03, and 80% having $M_n$ 7650, $M_w$ 31,500, D=4.12 (overall, $M_n$ 3430, $M_w$ 26,800). Precipitation of the product with aqueous methanol gave 8.46 g. Analysis of the copolymer showed 1.76% N, corresponding to 1.25 meq/g of N,N-dimethylaminoethyl methacrylate units. The recovered catalyst weighed 0.46 g. Infrared analysis of the recovered catalyst showed incorporation of PMMA.

Example 23

A. Preparation of Crosslinked Polystyrene Beads with Pendant Silyl Ketene Acetal Functional Groups

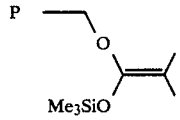

To a suspension of 12 g (16 meq) of aldehyde-substituted crosslinked polystyrene beads (prepared by the method of Ayres and Mann, Polym. Lett. 1965, 3, 505–508) in 140 mL of anhydrous THF was added 0.3 g (32.6 mmol) of lithium aluminum hydride. The solution turned green. After stirring at reflux for 12 h, the mixture was cooled, treated dropwise with 1 mL of water, 1 mL of 15% aqueous sodium hydroxide, and finally 3 mL of water. After 1 h the polymer was filtered, washed twice with 3 N HCl, 3 times with water, and twice with methanol, and then dried in a vacuum oven to give 12 g of hydroxymethyl polystyrene. IR analysis shows OH (strong) at 3570 cm$^{-1}$, and no C=O absorption. The same procedure used in Example 12 was used to convert 6 g of the hydroxymethyl polystyrene to 6.08 g of polymer with pendant silyl ketene acetal groups. Anal. found: Si 2.25% corresponding to 0.8 meq/g of Si. IR: 1705 cm$^{-1}$ (silyl ketene acetal), 1735 cm$^{-1}$ (ester).

B. Polymerization of MMA with Crosslinked Polystyrene Beads with Pendant Silyl Ketene Acetal Functional Groups To a stirred mixture of 0.5 g of crosslinked polystyrene beads with pendant silyl ketene acetal groups from Part A, 10 mL of THF, and 1.1 mL of MMA was added 40 μL of 0.38 M tetrabutylammonium m-chlorobenzoate in THF. A temperature rise of 0.4° was observed. After 2 h, a sample of the supernate was removed for analysis by NMR which showed residual MMA. The product was collected by filtration and extracted for 18 h in a Soxhlet apparatus with THF to give, after drying, 1.15 g of PMMA. grafted to polystyrene (65% yield). IR (KBr) showed chiefly PMMA with less polystyrene.

Example 24 - (effect of Acetonitrile on Polydispersity of PMMA Prepared with Supported m-Chlorobenzoate Catalyst To a stirred mixture of 200 mg of insoluble, crosslinked polystyrene-supported tributylmethylammonium m-chlorobenzoate of Experiment C-7, 70 mL of THF, 1 mL of acetonitrile, 0.8 mL (4 mmol) of 1-methoxy-1-trimethylsiloxy-2-methyl-1-propene and 0.71 mL (8 mmol) of benze was added 21.6 mL (200 mmol) of MMA. A slow temperature rise of 18° was observed. A sample of the supernate was removed after 2 h for analysis. NMR showed 50% residual monomer. GPC showed $M_n$=3110, $M_w$=10,600, $M_w/M_n$=3.425. After 18 h another sample was removed for analysis. GPC showed $M_n$=4940, $M_w$=11,200, $M_w/M_n$=2.266. The catalyst was removed by filtration, and the filtrate was evaporated to 16.63 g (83% yield) of PMMA. The polymer was purified by precipitation from methylene chloride with hexane. GPC: $M_n$=4630, $M_w$=9580, $M_w/M_n$=2.08. Analysis for N showed 0.05%. $(C_5H_8O_2)_{46}CH_2CN$ requires N=0.30%. Thus, little, if any chain transfer to acetonitrile occurred. In a similar manner, the supported m-chlorobenzoate catalyst was used for polymerization of MMA with 5 mL of added acetonitrile, and with no added acetonitrile. The principal effect of the acetonitrile is to lower the polydispersity of the PMMA. The results are summarized in Table I.

TABLE I

EFFECT OF ACETONITRILE ON POLYMERIZATION OF MMA WITH SUPPORTED m-CHLOROBENZOATE CATALYST

| Vol Frac MeCN | $\overline{M}_n$ | $\overline{M}_w$ | $\overline{M}_w/\overline{M}_n$ | Temperature Rise (°C.) | Yield % |
|---|---|---|---|---|---|
| 0 | 4,240 | 13,600 | 3.218 | 25 | 100 |
| 0.014 | 4,940 | 11,200 | 2.266 | 18 | 83 |
| 0.067 | 4,330 | 8,070 | 1.862 | 16 | 99 |

Example 25

An 8 cm column of beads of "Amberlyst" A-27 macroreticular ion-exchange resin, a polystyrene heavily crosslinked with divinyl benzene and containing quaternary ammonium chloride terminal groups, was treated with a solution of 250 mL of sodium acetate in 300 mL of distilled water to convert the anion from chloride to acetate. The column was then washed with 500 mL of water to remove excess sodium acetate.

A portion of the beads was placed in a 125 mL flask to which was added about 4.5 mL of MMA, then 0.5 mL of [(1-methoxy-2-methyl-1-propyl)oxy]trimethylsilane. After several days, the viscosity had increased substantially, and analysis confirmed the presence of PMMA; GPC: $M_n$ 3280.

Example 26 - Preparation of Crosslinked Polystyrene Beads with Pendant Silyl Ketene Acetal Functions A mixture of 1.25 g of anhydrous zinc chloride, 60 mL of dichloromethane, 5 g of chloromethylated polystyrene crosslinked with 1% divinylbenzene (200–400 mesh, Bio-Beads S-X1, 4.2 meq Cl/g, Bio-Rad Laboratories, Richmond, Calif.), and 10.4 g (30 mmol) of 1,2-bis(1-trimethylsiloxy-2-methyl-1-propenoxy)ethane was stirred for 18 h, filtered under argon, and washed with dichloromethane. The beads were extracted 5 times with tetrahydrofuran (THF). After drying in vacuo there was obtained 6.3 g of product. Anal Found: Si 2.00, Cl 6.11 which corresponds to 0.71 meq Si/g and 1.7 meq residual Cl/g. Infrared analysis (KBr) shows strong absorption at 1730 cm$^{-1}$ (saturated ester C=O), 1705 cm$^{-1}$ (silyl ketene acetal C=C), 1250 and 845 cm$^{-1}$ (SiMe) consistent with the structure

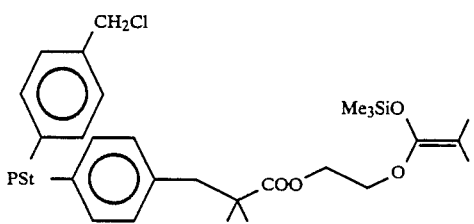

Example 27 - Preparation of a Crosslinked Polydimethylsiloxane with Silyl Ketene Acetal Functionality A. A mixture of 7 g of (15-18%)methylhydro-(82-85%)-dimethylsiloxane copolymer (MW 2000–2500, Petrarch Systems, Bristol, Pa., Cat. No. PS123.5), 4 mg phenothiazine (to inhibit any radical polymerization), 20 mg tris(triphenylphosphine)-rhodium chloride, and 1.5 mL trimethylolpropane trimethacrylate was heated at 85°, and an exothermic reaction caused the temperature to rise to 89°. The temperature slowly fell, and the solution gelled. After a total heating period of 1 h, the gel was mixed in a blender with hexane, filtered, and dried at 0.1 mm to give 5.88 g of solid polymer particles. To demonstrate that the crosslink sites were silyl ketene acetals rather than polymerized methacrylate groups, a sample of the polymer was suspended in about 10 mL of THF and treated with 2 drops of hydrochloric acid, whereupon the swollen suspension almost immediately gave a clear solution. A slurry of the solid polymer particles in chloroform-d was treated with a few drops of methanol and a drop of hydrochloric acid which produced a clear solution. NMR analysis cf the clear solution showed that there were 2.66 isotutyrate units per methacrylate unit, or that each trimethylolpropane trimethacrylate unit had generated 2.18 silyl ketene acetal groups and 0.82 residual methacrylate unit in the hydrosilation process. There were approximately 9.45 Si atoms per isobutyrate residue, or about 1 15 meq/g of silyl ketene acetal units.

B. The process of Part A was repeated on a three-fold scale with reaction time increased to 2 h. There was obtained a crosslinked polymer which was shown by NMR analysis of the hydrolysate to contain, for each trimethylolpropane trimethacrylate unit, 96% silyl ketene acetal, and 4% residual methacrylate unit.

Example 28 - Preparation of Silica-Containing Pendant Silyl Ketene Acetal Functionality To 50 g of silica gel (Merck, surface area 675 m$^2$/g) was added slowly thionyl chloride until a slurry was obtained. The mixture was gently refluxed for 18 h, and excess thionyl chloride was removed under reduced pressure. Then the product was heated at 115° at 0.1 mm for 2 h and then at 150° for 30 min. Titration of a 0.5 g-sample of the resulting chlorinated silica with standard 0.1M sodium hydroxide solution showed that the chlorine content was 2.16 meq/g. To a solution of 7 mL (50 mmol) of diisopropylamine in 100 mL of THF at 0° was added 50 mmol of 1.6M butyl lithium in hexane After 20 min at 0°, the solution was cooled to −78°, and 5.73 mL (50 mmol) of methyl isobutyrate was added. After 30 min at −78°, 10 g (21.6 meq of Cl) of the chlorinated silica was added. The mixture was allowed to warm to room temperature and stirred for 1 h. The product was filtered, washed with THF, extracted with THF and filtered. After drying there was obtained 12.1 g of silica containing pendant silyl ketene acetal functions. Elemental analysis showed 8.81% C, 1.81% H.

Comparative Experiment 1 - Preparation of Crosslinked Polystyrene-Supported Tetrabutylammonium Benzoate A suspension of 1 g of crosslinked polystyrene (1% crosslinked with divinylbenzene) containing 1.4 meq/g carboxylic acid groups (prepared from the corresponding aldehyde by the method of Frechet and Haque, *Macromolecules,* 8, 130 (1975)) in 15 mL of tetrahydrofuran and 3 mL of 1M tetrabutylammonium hydroxide in methanol was stirred 18 h, filtered, and washed with methanol and with tetrahydrofuran. The resin was extracted in a Soxhlet apparatus with tetrahydrofuran and dried IR: 1565 cm$^{-1}$ (RCOO−), 1700 cm$^{-1}$ (COOH). Anal found C 85.84, H 8.40, N 0.59% which corresponds to 0.42 meq/g of tetrabutylammonium.

Comparative Experiment 2 - Evaluation of Extracts of Polystyrene-Supported Acetate Catalyst in Catalysis of Polymerization of Methyl Methacrylate A. A mixture of 0.1 g of the polymer-supported acetate catalyst of Experiment C-2 and 30 mL of tetrahydrofuran was stirred for 1 h and then filtered (to remove the insoluble catalyst) into a flask containing 20 mL of tetrahydrofuran, 5.4 mL of methyl methacrylate, and 0.2 mL (1 mmol) of 1-methoxy-1-trimethylsiloxy-2-methyl-1-propene. Analysis of a sample using $^1$H NMR after 1 h showed the presence of monomer, and the absence of polymer After stirring overnight precipitation with aqueous methanol gave 0.98 g of PMMA. GPC: $M_n$ 21,100, $M_w$ 54,800, D=2.59. The $M_n$ shows no relationship to the ratio of initiator to monomer.

B. The procedure of Part A was followed except that the supported acetate catalyst was stirred for 1 h with a mixture of tetrahydrofuran and .2 mL of 1-methoxy-1-trimethylsiloxy-2-methyl-1-propene. $^1$H NMR-analysis of the monomer solution 1 h after addition of the filtrate and an additional 0 2 mL of 1-methoxy-1-trimethylsiloxy-2-methyl-1-propene showed the presence of monomer and the absence of PMMA. After 18 h, 1.3 g of PMMA was precipitated with aqueous methanol. GPC: $M_n$24,300, $M_w$ 63,400, D=2.6 The $M_n$ shows no relationship to the ratio of initiator to monomer.

Comparative Experiment 3 - Catalysis of Polymerization of Methyl Methacrylate with Crosslinked Polystyrene-Supported Tetrabutylammonium Phenylacetate of Experiment C-6(B)

The procedure of Example 16 was followed using 0.1 g of polymer-supported phenylacetate of Experiment C-6(B) instead of the polymer-supported acetate of Experiment C-2. Following an induction period of about 2.5 min, a rapid exothermic polymerization produced a 23° temperature rise in 1 min. A sample of the supernate was removed for analysis, and NMR showed 100% conversion of methyl methacrylate to PMMA. GPC: $M_n$ 4670, $M_w$ 7650, D=1.64 (theory $M_n$ 5100). Polymerization of methyl methacrylate in the second flask after removal of the catalyst by filtration and addition of 0.2 mL of 1-methoxy-1-trimethylsiloxy-2-methyl-1-propene was slower than in the first flask, but analysis of a sample of the solution showed 100% conversion to PMMA. GPC: $M_n$ 5090, $M_w$ 6780, D=1 49. IR analysis of the recovered catalyst showed little, if any, grafting of PMMA to the catalyst

Comparative Experiment 4 - Evaluation of Extracts of Polystyrene-Supported Tetrabutylammonium Phenylacetate of Experiment C-6(B)

A. The procedure of Comparative Experiment 2(A) was followed using 0.1 g of polymer-supported tetrabutylammonium phenylacetate of Experiment C-6(B) instead of the polymer-supported acetate catalyst of Experiment C-2. No polymerization of methyl methacrylate was detected after 18 h.

B. The procedure of Comparative Experiment 2(B) was followed using 0.1 g of polymer-supported tetrabutylammonium phenyl acetate of Experiment C-6(B), instead of the polymer-supported acetate catalyst of Experiment C-2. Exothermic polymerization of the methyl methacrylate occurred in the second flask without the need to add additional silyl ketene acetal initiator. A temperature rise of 11.2° occurred during a period of 18.5 min. Analysis of the reaction mixture showed that conversion of methyl methacrylate to PMMA was 100%. GPC: $M_n$ 23,900, $M_w$ 36,000, D=1.5.

Comparative Experiment 5 - Failure of Polymer-Supported m-Chlorobenzoate and Polymer-Supported Silyl Ketene acetal to Polymerize Methyl Methacrylate A mixture of 0.5 9 of crosslinked polystyrene containing pendant silyl ketene acetal groups prepared by the procedure of Example 10A (1.g meq/g of Si), 1.08 mL of methyl methacrylate, 89 μL of benzene (internal standard for NMR calibration of monomer concentration), 50 mg of crosslinked polystyrene-supported m-chlorobenzoate catalyst of Experiment C-7 and 10 mL of THF was stirred at room temperature for 22 h. Analysis of a sample of the supernate by NMR showed that no PMMA was present in solution and that there was no detectable reduction in the concentration of methyl methacrylate. Then 2 mL of methanol was added, and the polystyrene was isolated by filtration. The filter cake was extracted in a Soxhlet apparatus with THF and dried to give 0.57 g of polymer. Infrared analysis showed by the absence of any absorption at 1265 cm$^{-1}$ that no PMMA was grafted to the support.

UTILITY EXAMPLES

Reagents for Examples 29-31

Lambda phage DNA, available from Boehringer Mannheim as a Hind III restriction enzyme digest, comprises a mixture containing six DNA fragments ranging in size from 562 to 23,130 base pairs Radiolabeled tracer DNA was prepared by either end-labeling the Lambda DNA fragments with 32P-ATP using the procedure of O'Farrell, Bethesda Research Laboratory publication Focus, 3(3), (1981), or by E. coli polymerase nick translation of the Lambda DNA using 3H-TTP according to the procedure of Maniatis et al., Pro. Natl. Acad. Sci., 72, 1184 (1975). Generally, specific activities of the resulting labeled preparation were ca. $10^7$ cpm/μg of DNA.

A blocking solution of Salmon Sperm DNA (Sigma Chemical Company) was prepared by sonicating the DNA (10 mg/mL) in a pH 7.0 saline sodium citrate buffer (SSC, twice normal strength, i.e. 2X) containing 17.4 g of sodium chloride, and 8.82 g of sodium citrate per liter. The blocking solution was dispensed into aliquots for storage and sterilized by autoclaving.

Denhart's solution (50 times normal strength, i.e. 50X) was prepared by dissolving Ficoll-400 (5 g), polyvinylpyrrolidone (5 g), bovine serum albumin (5 g Pentax fraction V) in purified water (1 liter).

A wash solution (SSPE) containing a 0.02M phosphate buffer, ethylene diamine tetraacetic acid (EDTA) and 0.1% sodium dodecyl sulfate (SDS) was prepared by dissolving sodium chloride (8.76 g), sodium dihydrogen phosphate monohydrate (1.38 g), EDTA (0.37 g) and sodium dodecyl sulfate (1.0 g) in purified water (1.0 liter) and adjusting the pH to 7.4.

Example 29 - Complexation of Lambda DNA on GTP Grafted Solids 2.0 μg Of radiolabeled Lambda DNA (1.9×10$^5$ cpm/μg) was separated into single strands by denaturing with 1 0M sodium hydroxide (0.15 mL). After 5 min. at room temperature, the DNA solution was neutralized with an equal volume of 2M ammonium acetate. The resulting target DNA sample was then placed in an ice bath until use.

To evaluate the extent of DNA interaction with the GTP grafted solids, the target DNA samples, prepared above, were equilibrated with 10 mg quantities of the N,N-dimethylaminoethyl methacrylate (DMAEMA)-grafted beads from Example 3 As controls, equal amounts of target DNA were equilibrated with equal quantities of the MMA-grafted beads from Example 2, or ungrafted beads. The control materials were expected to provide little or no DNA attachment in comparison to the DMAEMA grafted solids. After shaking the bead preparations at 4° for 15 min., the bead preparations were first equilibrated (5 min.) with a blocking solution of 0.1% Salmon Sperm DNA in SSC (2X) buffer solution and then washed three times with SSC (2X) buffer solution to dilute and remove excess target DNA.

Portions of the three bead preparations were then removed and dried and their radioactive contents were determined in order to establish the extent of DNA complexation with the beads. The results, summarized in Table II (DNA Binding, % DNA Target Bound), show that the DMAEMA-grafted solids bound a substantially greater percentage of the target DNA in the original sample than either of the control solids.

Example 30 - Retention of Lambda DNA on GTP Grafted Supports

For probe hybridization applications, the target DNA must first bind to the solid and then remain affixed to the solid surface under stringent wash conditions designed to remove non-specifically hybridized probe.

To examine the degree of DNA retention on the solids under stringent wash conditions, the solids of Example 29 were equilibrated at 65° for 18 h in Denhart's solution (5X normal strength) containing 31% formamide, 0.1% SDS, and 0.5M sodium chloride The solids were then washed with SSC (2X) buffer solution and samples of the three bead preparations taken and dried for determination of radioactive content. As shown in Table II (DNA Binding, % Target DNA Retention), the GTP-grafted DMAEMA beads retained significantly higher DNA content than control solids.

These findings confirm that GTP grafting with DMAEMA monomer not only altered the surface properties of the beads but produced a solid which is effective in promoting both DNA complexation and retention.

Example 31 - Hybridization of Lambda DNA on GTP Grafted Supports

Hybridization experiments were performed using radiolabeled Lambda probe DNA to determine if the target DNA on the solids was appropriately oriented to facilitate annealing with complementary DNA strands.

The solids (10 mg) from Example 29, coated with target DNA and blocked with Salmon Sperm DNA, were equilibrated at 50° for 18 h with 32P end-labeled single stranded Lambda DNA probe (2 $\mu$g, $2 \times 10^6$ cpm/$\mu$g) in a hybridization buffer containing SDS (0.1%), formamide (31%), Denhart's solution (10 X) in SSC (3X) buffer solution at pH 7. After hybridization the solids were washed with SSPE (0.1X) buffer containing SDS (0.1%) at 50° to remove unhybridized probe. The solids were then harvested and counted to determine the radioactive probe content. The efficiency of hybridization was computed by dividing total probe DNA bound by the total target DNA retained on the solids.

The results, summarized in Table II (Probe Hybridization), show that significantly greater amounts of probe were hybridized to the DMAEMA-grafted solids than to the control solids. Moreover, hybridization efficiency suggested that target DNA bound to the GTP grafted DMAEMA solids was available and favorably oriented on the surface for hybridization with probe.

TABLE II

| | | Lambda DNA Interation with GTP Grafted and Control Solids | | | | |
|---|---|---|---|---|---|---|
| | | DNA Binding | | | Probe Hybridization | |
| Particle Type | Grafting Monomer | Target DNA Bound (ng) | % Target Bound | % Target DNA Retention | Probe Bound (ng) | Hyb. Efficiency (%) |
| CMS | DMAEMA | 740 | 71 | 33 | 94 | 14 |
| CMS | MMA | 59 | 6 | 0.11 | 0.32 | |
| CMS | | 37 | 4 | 0.07 | 0.33 | |

CMS: chloromethyl styrene

We claim:

1. Group Transfer Polymerization (GTP) process for preparing a "living" polymer, the process comprising contacting under polymerizing conditions in a polymerization medium, at least one acrylic or maleimide monomer with an initiator which is a tetracoordinate organosilicon, organotin or organogermanium compound having at least one GTP inititaing site and a catalyst which is, or is a source of, an anion selected from the group consisting of bifluoride, fluoride, cyanide, axide or a selected oxyanion, or a selected Lewis acid or Lewis base, the process further characterized in that the initiator is chemically attached to a solid support that is insoluble in the polymerization medium.

2. Process of claim 1 wherein the support is crosslinked polystyrene or crosslinked polydimethylsiloxane.

3. Process of claim 1 wherein the initiator is a tetracoordinate organosilicon compound.

4. Process of claim 3 wherein the initiator is a silyl ketene acetal.

5. Process of claim 4 wherein the initiator contains at least two initiating sites.

6. Process of claim 1 wherein the monomer is (meth)acrylonitrile or a (meth)acrylate ester or amide.

7. Process of claim 6 wherein the ester is methyl methacrylate, N,N-dimethylaminoethyl methacrylate, methyl or ethyl acrylate, and the amide is N,N-dimethylacrylamide.

8. Process of claim 7 wherein the ester is N,N-dimethylaminoethyl methacrylate.

* * * * *

UNITED STATES PATENT AND TRADEMARK OFFICE
CERTIFICATE OF CORRECTION

PATENT NO. : 4,940,760         Page 1 of 2
DATED      : JULY 10, 1990
INVENTOR(S): BOETTCHER ET AL.

It is certified that error appears in the above-identified patent and that said Letters Patent is hereby corrected as shown below:

On the title page, Item [75] Inventor: delete --Ira B. Dicker--

Column 16, line 26, delete "COO31" and insert in its place -- COO- --.
Column 17, line 28, delete "1 36" and insert in its place -- 1.36 --.
Column 17, line 28, delete "10 4 g" and insert in its place -- 10.4 g --.
Column 17, line 33, delete "1 86%" and insert in its place -- 1.86% --.
Column 19, line 51, delete "SilYl" and insert in its place -- Silyl --.
Column 21, line 62, delete "$ilyl" and insert in its place -- Silyl --.
Column 24, line 6, delete "$oxhlet" and insert in its place -- Soxhlet --.
Column 32, line 34, delete "axide" and insert in its place -- azide --.

UNITED STATES PATENT AND TRADEMARK OFFICE
CERTIFICATE OF CORRECTION

PATENT NO. : 4,940,760
DATED : July 10, 1990
INVENTOR(S) : Boettcher, et al

It is certified that error appears in the above-indentified patent and that said Letters Patent is hereby corrected as shown below:

Column 30, line 41 and 42, delete "denaturing with 1 OM sodium" and insert in its place -- denaturing with 1.0M sodium --.

Signed and Sealed this

Sixteenth Day of August, 1994

*Attest:*

BRUCE LEHMAN

*Attesting Officer*   *Commissioner of Patents and Trademarks*